United States Patent [19]
Watt et al.

[11] Patent Number: 5,433,412
[45] Date of Patent: Jul. 18, 1995

[54] MEDICAL WASTE INFECTIOUS SUBSTANCE DISPOSAL AND TRANSPORTATION SYSTEM

[76] Inventors: Ramon C. Watt, 215 Continental Dr., Lockport, N.Y. 14094; C. Ray Goff, Jr., 7500 Fiesta Way, Raleigh, N.C. 27615

[21] Appl. No.: 229,214

[22] Filed: Apr. 18, 1994

[51] Int. Cl.[6] .......................... B65F 1/16; B65D 85/24
[52] U.S. Cl. ..................................... 206/370; 206/438; 220/408
[58] Field of Search ............. 206/366, 370, 438; 220/908, 408

[56] References Cited

U.S. PATENT DOCUMENTS

| | | | |
|---|---|---|---|
| 4,494,652 | 1/1985 | Nelson et al. | 206/370 |
| 4,520,926 | 6/1985 | Nelson | 206/366 |
| 4,560,069 | 12/1985 | Simon | 206/591 |
| 4,576,281 | 3/1986 | Kirksey | 206/366 |
| 4,600,112 | 7/1986 | Shillington et al. | 206/366 |
| 4,809,850 | 3/1989 | Laible et al. | 220/908 |
| 5,031,767 | 7/1991 | Bruno | 206/370 |
| 5,067,223 | 11/1991 | Bruno | 206/366 |
| 5,183,156 | 2/1993 | Bruno | 206/370 |
| 5,261,551 | 11/1993 | Watt | 220/256 |

*Primary Examiner*—Jimmy G. Foster
*Attorney, Agent, or Firm*—Terry M. Gernstein

[57] ABSTRACT

Medical waste, i.e., infectious material such as needles and sharps, are contained in a system that meets Federal Regulations concerning the storage and disposal of medical waste, while also meeting Federal Regulations concerning transportation of such medical waste, yet also is environmental friendly upon disposal. The system includes a one-piece, monolithic plastic bottle contained in a unitary metal outer container, with a one-way plug located in a neck of the bottle to permit items to enter the bottle but to prevent those items from leaving the bottle via the neck. A closure is attached to the neck, with a lid and an overcap ring covering the closed bottle for shipping. Adhesive material can be used to further seal the system, with the container being placed in a corrugated carton that is then sealed with further adhesive for transportation.

20 Claims, 4 Drawing Sheets

MEDICAL WASTE INFECTIOUS SUBSTANCE DISPOSAL AND TRANSPORTATION SYSTEM

TECHNICAL FIELD OF THE INVENTION

The present invention relates to the general art of containers, and to the particular field of hazardous waste containers, and specifically to containers for medical waste/infectious substance.

BACKGROUND OF THE INVENTION

In recent years, Federal Agencies, specifically, OSHA, have developed Blood Borne Pathogen Regulations for the workplace (see, e.g., 29 CFR). Furthermore, the Department of Transportation has developed strict packaging standards for the safe transport of infectious material (see, e.g., 49 CFR). According to definitions included in these regulations, all used needles and sharps must be treated as infectious materials.

The packaging requirements for an infectious material Package is that it be a dual container system. One package must be capable of withstanding an internal pressure of 95 KPA (13.7 pounds) for thirty minutes, and the second package must be leak tight and capable of passing 30 KPA (4 pounds). This package must withstand drop tests of approximately thirty feet, if the inside of the container is plastic, it must be preconditioned for twenty-four hours at 0° F. and then dropped, and the overall package must be submerged in water for five minutes and dropped. In addition, there is a penetration test using a sharp steel rod weighing fifteen pounds that drops in free fall on two orientations of the final package. The Infectious Package must pass all of these tests.

In addition to the transportation problems, there is a problem of handling packages while they are being used and the most common failure of existing packages is inadvertent needle sticks from needles protruding through some portion of the package.

The art contains many examples of packages that can be used to transport various types of waste. However, many of these packages are designed for on-site disposal of sharps, and are incapable of passing the required tests for transporting off site and many of these known packages are made of plastic or fiberboard material which makes them eligible for the inadvertent pin stick while being used. While the art also includes other containers for packaging hazardous materials, such containers are not suitable for sharps.

Therefore, there is a need for a medical waste disposal system that is safe and meets all of the current regulations for transporting the package to its final disposal site.

Still further, many Federal and State Agencies have strict requirements regarding waste and the degradability thereof. Therefore, in addition to meeting the above-discussed regulations, a medical waste disposal system must also meet environmental regulations as well. Accordingly, there is a need for a medical waste disposal system that meets regulations associated with medical waste as well as environmental standards. Heretofore, the systems known to the inventors have not been able to satisfy all of these requirements.

Many known containers are made of metal. Metal can be expensive, and difficult to form and manufacture in a cost-effective manner. Due to this problem, variations in design may be difficult and not undertaken. Accordingly, there is a need for a medical waste disposal system that can be manufactured in a cost-effective manner, and can be altered as necessary without incurring undue costs.

OBJECTS OF THE INVENTION

It is a main object of the present invention to provide a medical waste disposal system.

It is another object of the present invention to provide a medical waste disposal system that meets all of the current regulations for transporting the package to its final disposal site.

It is another object of the present invention to provide a medical waste disposal system that meets all of the current regulations for transporting the package to its final disposal site and that is environmentally friendly when disposed.

It is another object of the present invention to provide a medical waste disposal system that can be manufactured, and once manufactured, changed, in a cost-efficient manner.

SUMMARY OF THE INVENTION

These, and other, objects are achieved by a medical waste disposal system that includes a one-piece, monolithic plastic bottle securely positioned inside a metal outer container, with closure means on the outer container covering the bottle, with both items being sealed closed and placed in a double wall corrugated carton, which is sealed for shipping and disposal. The outer container is metal and protects against pin sticks. The system is capable of passing all the Infectious Test Criteria as set out in 49 Code of Federal Regulations, and is also environmentally friendly when incinerated, because the package is reduced to sterilized ash.

The one-piece nature of the plastic bottle ensures that pressure and submergence requirements will be met, and the metal outer container ensures that impact and penetration requirements will be met, while each wall of these elements assists and reinforces the adjacent wall of the other element to produce a synergistic effect. Further, since the bottle is formed of plastic, its parts, such as its neck, can be varied as necessary to satisfy requirements of various applications without incurring undue costs as might be associated with other materials, such as metal. The bottle can be plastic because it is surrounded by metal; whereas the outer container can be metal because it has a one-piece plastic bottle inside, thus producing the just-mentioned synergistic effect. The outer container is unitary as opposed to the one-piece construction of the bottle, and thus is manufactured with seams and the like.

BRIEF DESCRIPTION OF THE DRAWING FIGURES

DETAILED DESCRIPTION OF THE PREFERRED EMBODIMENT OF THE INVENTION

Figure 1:
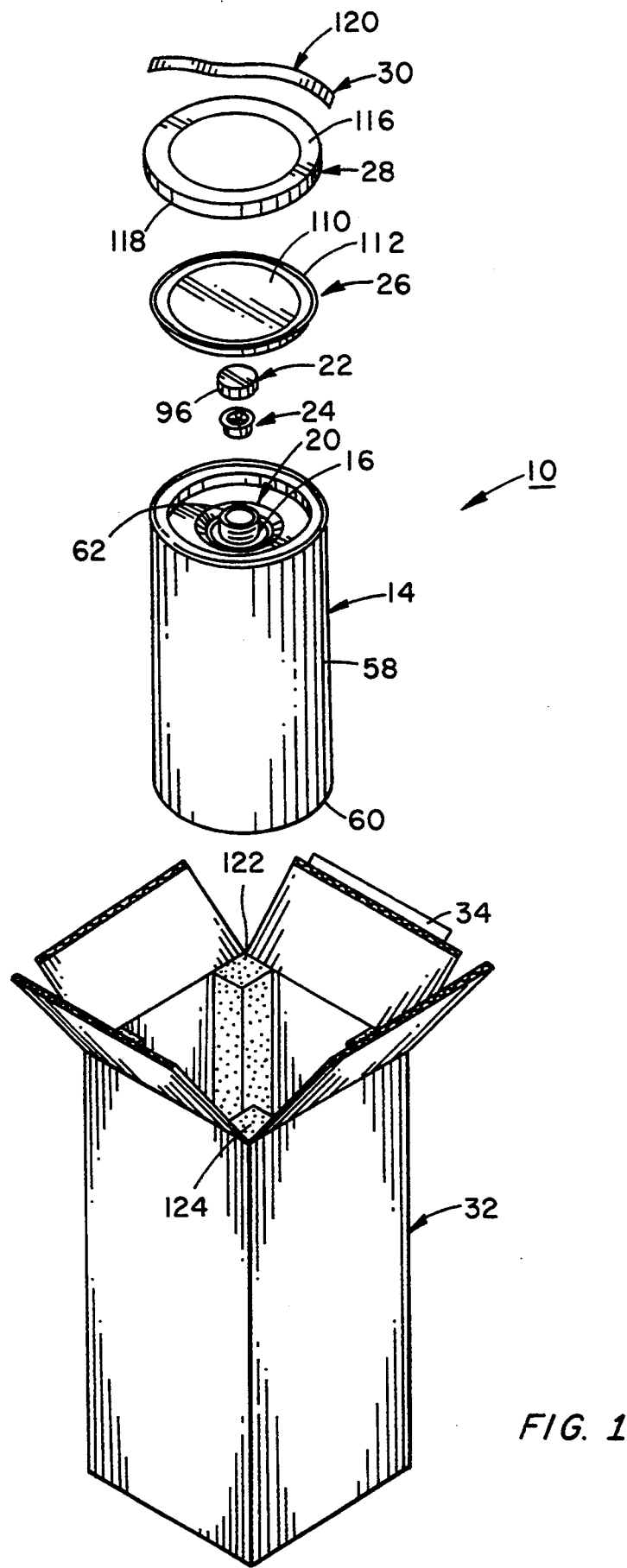
FIG. 1 is an exploded perspective of the medical waste disposal system embodying the present invention.

Shown in the Figures is a system 10 for containing and disposing medical waste and which meets all Infectious Test Criteria as well as current regulations for transporting this package to its final disposal site, yet which is still environmentally friendly for disposal.

System 10 includes, broadly, a bottle 12 that is securely positioned in an outer metal container 14 with a bottle neck 16 extending through a neck-receiving opening 18 in an insert element 20 to receive a threaded closure 22 to close the bottle. A one-way plug 24 is located in neck 16 and permits items, such as needles, to move into the bottle, but which prevents those items from moving back through the neck out of the bottle. System 10 further includes a lid 26 that is surmounted on container 14 along with an overcap ring 28, which is attached to the container by friction elements on the ring and on the container. Tape 30 is also used to further seal ring 28 to the container. Once assembled, the container/bottle combination is placed in a doublewall corrugated carton 32, which is further sealed with tape, such as tape 34.

Specifically, bottle 12 is one-piece and monolithic and is formed of high density polyethylene and includes a bottom wall 40 connected to a cylindrical sidewall 42 at a bottom corner 44. Sidewall 42 is connected to a top wall 46 by a top corner 48, with neck 16 being mounted on the top wall. The polyethylene material used to form bottle 12 is flexible so the bottle can have its outer diameter as measured on cylindrical sidewall 42, decreased by compression. Top wall 46 is conical, with neck 16 being located near the center and top apex of that wall. Top wall 46 includes a plurality of ribs 50 that are flexible and extend radially outward from neck 16 so top wall 46 is collapsible in direction 52 arid in direction 54 so the bottle can have its outside diameter decreased for a purpose that will be understood from the teaching of the ensuing disclosure. Ribs 50 provide flexibility to the top wall yet also provide reinforcing strength thereto, and make top wall 46 weblike. It is noted that neck 16 has an outer diameter which is small compared to the outer diameter of bottle 12 adjacent to the neck. In a preferred form of the bottle, neck 16 has an outer diameter of 38 mm, and bottle 12 has an outer diameter measured adjacent to the neck, of 6⅜ inches. The relatively small outer diameter of neck 16 contributes to the pressure resisting capabilities of bottle 12. However, because bottle 12 is formed of plastic, the size of neck 16 can be changed without incurring excessive costs.

Because the combination of bottle 12 and container 14 defines a double walled container having a one-piece, monolithic plastic inner wall abutting a metal outer wall, the combination can meet pressure and immersion requirements of Federal Regulations associated with medical waste/infectious material transportation and disposal as well as impact and penetration requirements of those regulations. Pressure and immersion requirements are met because the wall of a one-piece, monolithic plastic bottle is reinforced by a strong metal wall of a metal outer container, and impact, drop and penetration requirements are met because a metal wall is strengthened from the inside by a plastic wall. Still further, the one-piece nature of the bottle permits the combined system to meet submergence requirements. Thus, each wall assists and reinforces the other, and a synergistic effect is realized because the combination is stronger and more integral than the sum of the parts.

Bottle 12 is positioned in metal outer container 14 in the assembled system. Container 14 is unitary and includes a bottom wall 56 attached to a cylindrical sidewall 58 by a double seam at bottom corner 60. Sidewall 58 has an outer diameter that is slightly smaller than the outer diameter of bottle sidewall 42 so the bottle must be compressed to be forced into the outer container. This force fitting of bottle 12 into outer container 14 results in the bottle be securely held in place once it is in the outer container. The bottle will not rotate or move once it is in the outer container and the two elements, bottle 12 and container 14, will reinforce and support each other so each enhances the properties of the other. The collapsible top wall 46 of the bottle permits the bottle to be collapsed sufficiently to be forced into the outer container. The metal outer container provides integrity against pressure and fully jackets the bottle in the event of an explosion thereby further enhancing the overall performance of system 10.

Figure 6:
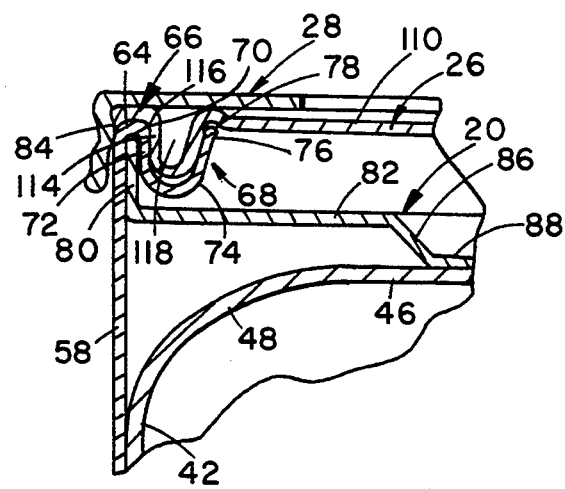
FIG. 6 is an enlarged view of the connections holding the insert element in the metal container, and an overcap ring to the metal container over the lid.
Figure 8:
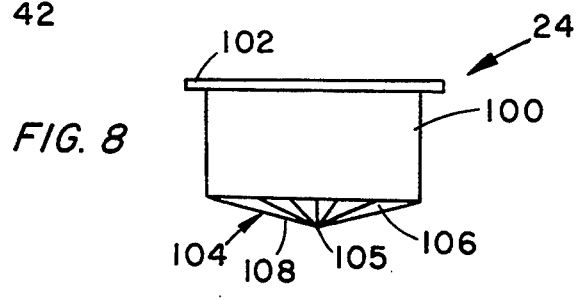
FIG. 8 is a perspective of a one-way plug used in the system to permit items to be placed in the system but will prevent those same items from moving out of the system.

Once the bottle is in place in outer container 14, the plane containing top rim 62 of neck 16 is beneath a plane containing top rim 64 of container sidewall 58 so the bottle is completely located within the outer container. As shown in FIG. 6, a double seam 66 connects a top element 68 to sidewall 58. Top element 68 includes an annular portion 70 extending radially inward from seam 66, a shoulder 72 extending downward from annular portion 70 and connecting annular portion 70 to a second annular portion 74 which extends radially inward from the shoulder 72. A second shoulder 76 is connected to second annular portion 74 and extends upward to at or near the plane containing first annular portion 70 where it is connected to a third annular portion 78 that extends radially inward from the second shoulder 72. Top element 68 thus extends radially inward from the sidewall 58 to partially cover the top of the container. The seams, shoulders and annular portions of top element 68 co-operate to define a portion of an attachment between outer container 14 and lid 26 as well as overcap ring 28 which have similar elements that co-operate with these seams, shoulders and annular portions. Top element 68 forms part of container 14 and is connected thereto by double seam 66.

Insert element 20 is received in the outer container to slide axially of that outer container sidewall 58, and includes a cylindrical sidewall 80 that extends from a planar annular section 82 to a top rim 84. Top rim 84 engages first annular portion 70 and rim 64 to prevent insert element 20 from exiting the outer container. When bottle 12 is in place in container 14, top 46 engages insert element 20 and biases that insert element in direction opposite to direction 52, that is, in a direction axially outward of container 14. This outward bias would force the insert element out of the container, except for the engagement between top rim 84 and rim 64. Annular section 82 extends radially inward from sidewall 80 to a shoulder 86 that extends downward and radially inward from that annular section to an annular section 88 that extends in a plane spaced from the plane containing section 82 and extends radially inward from shoulder 86. Neck-receiving opening 18 is defined by an inner rim of section 88. A plurality of channels 92 are defined in section 88 to extend radially from neck-receiving opening 18 to shoulder 86. The various elements of insert 20 are sized so outer rim 84 engages annular portion 70 and annular section 88 engages top wall 46 of bottle 12 when the bottle is in place in the container. The flexibility of top wall 46 permits the bottle to be slightly compressed in direction 52 to make sure the bottle is securely held in place in the container against axial movement. The radial compression of bottle 12 prevents the bottle from rotating once it is in place. In this manner, the bottle will be securely held in position within the container.

Figure 7:
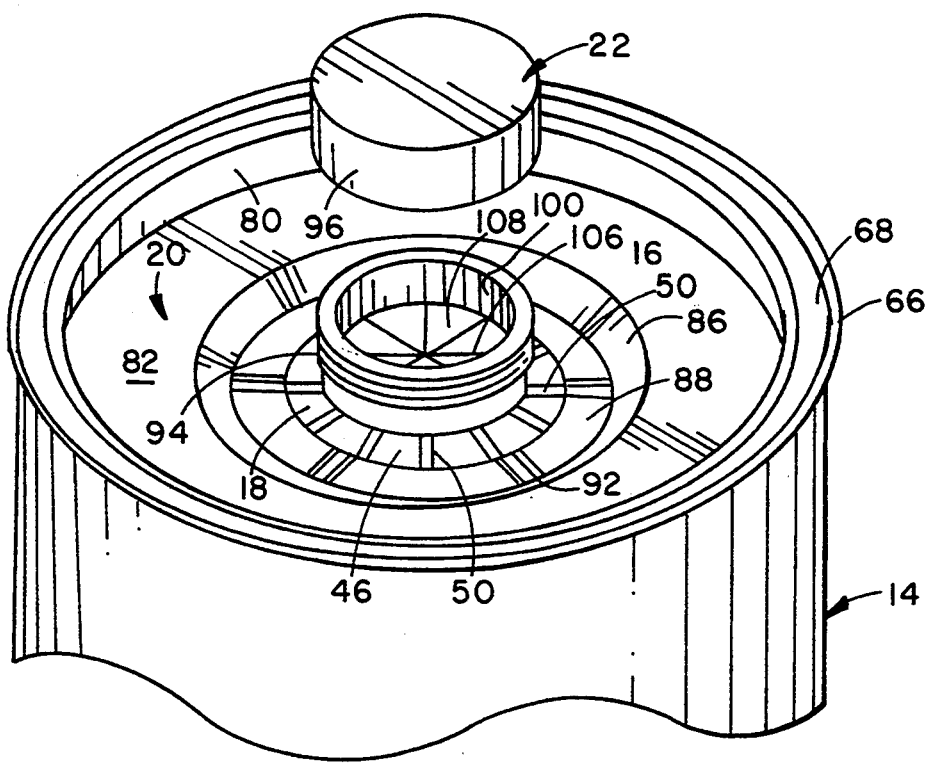
FIG. 7 is a top perspective view showing the metal container with the bottle therein and an insert element in place.
Figure 2:
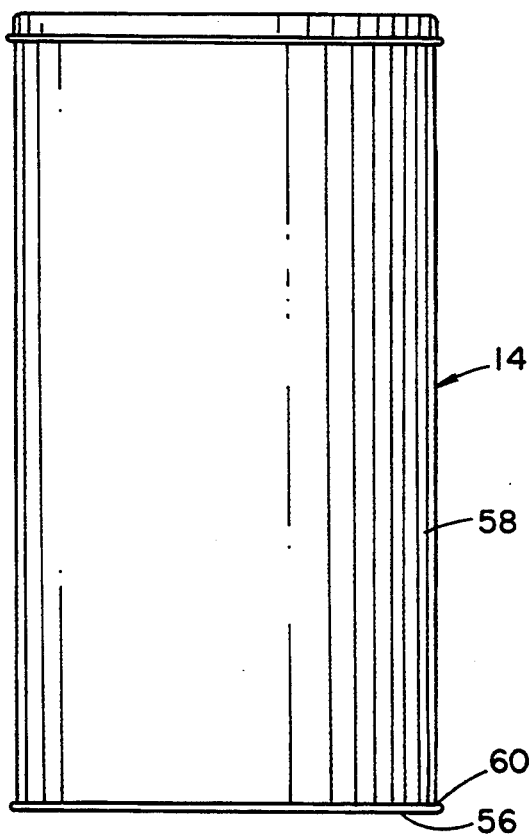
FIG. 2 is a side elevation view of a metal container used in the disposal system.
Figure 5:
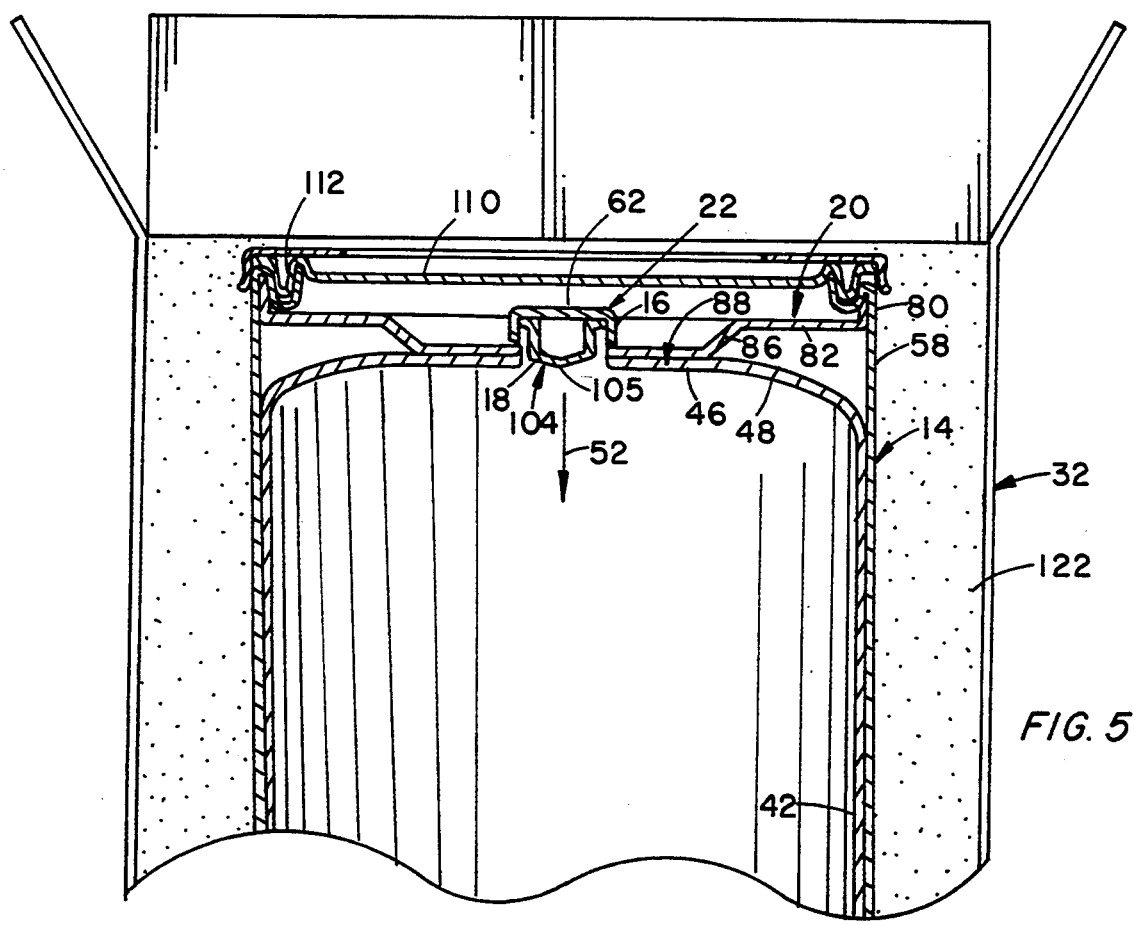
FIG. 5 is an elevation view of a bottle and metal container located in a packing carton, the bottom being omitted for the sake of convenience of illustration.

As shown in FIGS. 5 and 7, when bottle 12 is in place in the container, neck 16 is received through neck-receiving opening 18 with thread 94 on neck 16 exposed above annular section 88. Closure cap 22 has a thread on the inside of wall 96 that cooperatively engages thread 94 to hold closure 22 on neck 16 and close bottle 12. Bottle 12 and container 14 are sized so cap 22 is located inside container 14 beneath the plane containing rim 68 when the closure is on neck 16.

One-way plug 24 is received in neck 16, as is shown in FIGS. 5 and 7. Plug 24 permits needles and like medical waste to be inserted into bottle 12 via neck 16, but will prevent those items from moving out of the bottle via neck 16. As shown, plug 24 includes a sidewall 100 that is sized to frictionally engage the inside surface of neck 16 to hold plug 24 in place in the neck. Sidewall 100 has a top rim 102 that engages top rim 62 of neck 16 to help hold plug 24 in place on the neck. Plug 24 also includes a conical bottom wall 104 that extends from sidewall 100 downwardly and radially inward to form an apex 105 that is located at or near the center of neck 16 when plug 24 is in place in the neck. A plurality of slits 106 are defined in bottom wall 104 to divide that bottom wall into a plurality of triangular sections or flaps, such as section 108, each having an apex located at the center of the bottom wall and having an arcuate base defined by the intersection of the bottom wall and the sidewall 100.

Plug 24 is made of flexible material, such as a medium density polyethylene, and the triangular sections 108, are thus flexible. The sections 108 are contiguous and will flex downwardly in direction 52 to permit an item to move in direction 52 into the bottle via neck 16. However, the conical shape of bottom wall 104 and the orientation of the apexes of sections 108 adjacent to each other and at the center of neck 16 causes the sections 108 to contact one another and prevent those sections from flexing in a direction opposite to direction 52. In this way, the plug acts as a one-way plug by permitting items to move in direction 52 but preventing movement of items in a direction opposite to direction 52. Furthermore, one-way plug 24 acts as a bottle closure even when closure 22 is not in place on neck 16.

Lid 26 is metal and is secured to the outer container for shipping. Lid 26 includes a central planar section 110 connected to a shoulder 112 that extends downward past section 110 and outward and connects that section to a shoulder 114. Shoulder 114 extends upward past section 110 and outward and is surmounted by rim 116 that is located in a plane containing the top of shoulder 112. An annular gap 117 is defined between shoulders 112 and 114. Lid 26 is attached to the container 14 in covering relation thereto.

Overcap ring 28 fits over lid 26 to further hold that lid in place. Overcap ring 28 is fully described in U.S. Pat. No. 5,261,551, and the description therein is incorporated herein by reference. Accordingly, no further description of overcap ring 28 will be presented herein except to mention that it includes an annular section 116 that is connected to a sidewall 118 and engages lid 26 and container sidewall 58 to hold the lid in place on container 14. This engagement further secures the closed nature of the system 10.

Several, preferably three, strips of tape 120 are placed over sidewall 118 and on sidewall 58 to further secure ring 28 to container 14. The preferred form of tape 120 is manufactured by 3M Company as product number 375.

Once assembled, the combined bottle and container, are placed in carton 32 which has end caps 122 and 124 therein. The end caps are formed of expanded polystyrene (EPS) foam. The carton is shown in FIG. 1, and the end caps keep the container away from all sides of the corrugated carton. The carton is closed, and sealed with further strips of tape 134.

Figure 9:
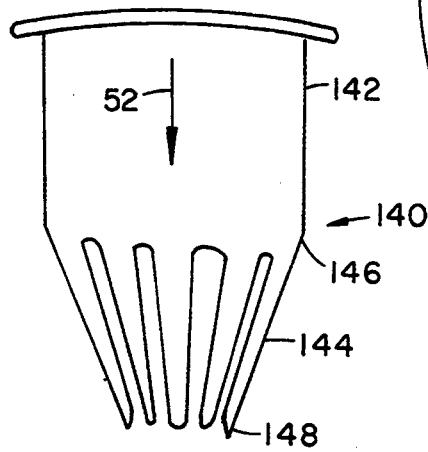
FIG. 9 shows a second form of the one-way plug.
Figure 4:
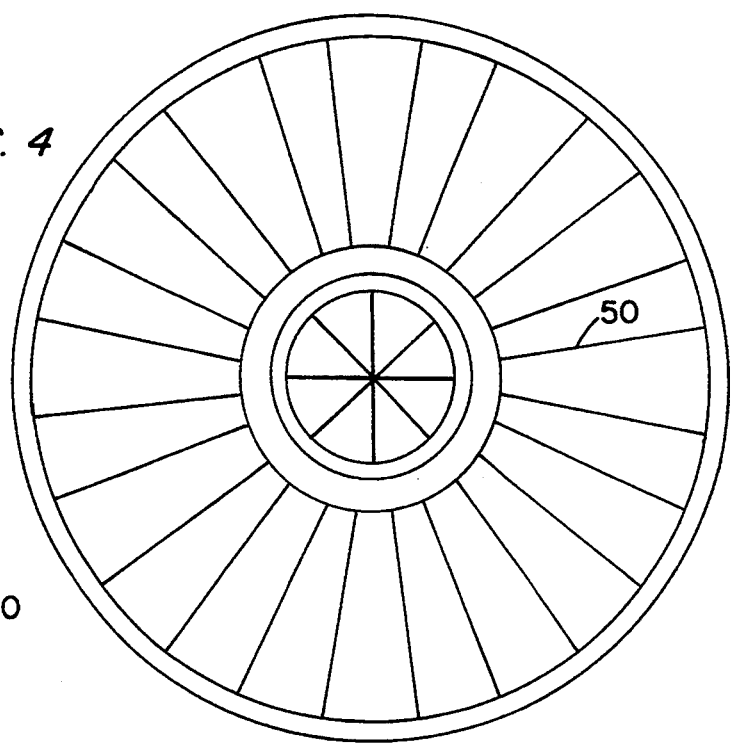
FIG. 4 is a top plan view of the bottle shown in FIG. 3.
Figure 3:
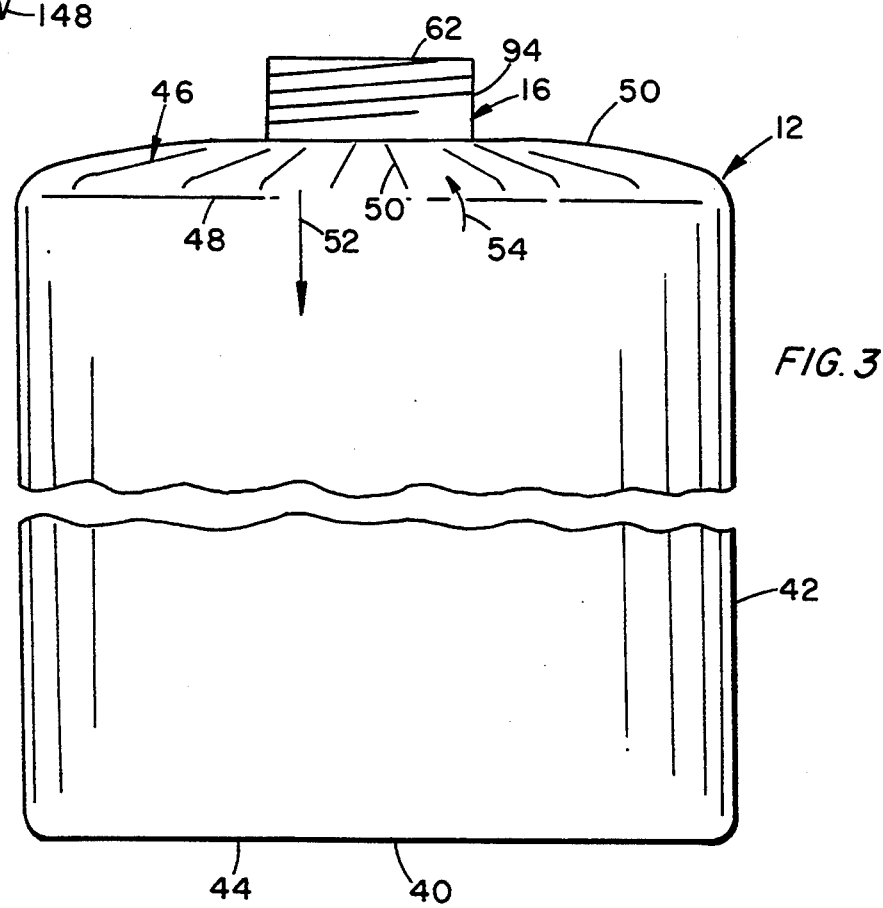
FIG. 3 is an elevation view of a bottle used in the disposal system, the bottle being broken for the sake of convenience of illustration.

Shown in FIG. 9 is a second form of the one-way plug used in system 10. Plug 140 includes a cylindrical body 142 having a rim 102 on one end thereof, and spaced apart fingers 144 on the other end thereof. Fingers 144 have a proximal end 146 connected to the body and extend downwardly and inwardly of the body, but have the distal ends 148 thereof spaced apart. Operation of plug 140 is similar to operation of plug 24 whereby items passing in direction 52 move past fingers 144, but items moving in the opposite direction will not pass by the plug. Preferably, plug 140 is formed of low density polyethylene or other similar material.

It is understood that while certain forms of the present invention have been illustrated and described herein, it is not to be limited to the specific forms or arrangements of parts described and shown.

We claim:

1. A system for containing and disposing medical waste/infectious material comprising:
   A) a bottle which includes
      (1) a sidewall,
      (2) a collapsible top wall, and
      (3) a neck;
   B) an outer container for enclosing said bottle and which includes
      (1) a sidewall having an inner diameter slightly smaller than the outer diameter of said bottle sidewall whereby said bottle is prevented from moving when it is in place within said outer container, and
      (2) a bottom wall;
   C) an insert element having a central section and a neck-receiving opening in said central section, said insert element being slidably received in said container and positioned for said neck-receiving opening to receive said bottle neck when said bottle is in place in said outer container;
   D) a one-way plug means in said bottle neck for permitting items to be inserted into said bottle and preventing those items from exiting from said bottle via said neck;
   E) a closure element for closing said neck;

F) a lid;

G) means for attaching said lid to said outer container in covering relation to said bottle;

H) an overcap ring; and

I) means for holding said overcap ring on said outer container in covering relationship to said lid.

2. The system defined in claim 1 wherein said outer container is metal.

3. The system defined in claim 1 wherein said one-way plug includes a sidewall and a plurality of flaps in a bottom wall.

4. The system defined in claim 3 wherein said bottom wall of said one-way plug is conical, with said flaps being triangular and each having an apex located near an apex of said conical bottom wall and a base, said flaps extending downwardly into said neck when said plug is in place in said neck.

5. The system defined in claim 1 wherein said insert element includes a wall, an annular section extending in a first plane radially inward from said wall, a shoulder extending out of a plane containing said annular section and radially inward from said annular section, a second annular section extending radially inward from said shoulder in a plane spaced from said first plane, said central section being in said second annular section.

6. The system defined in claim 1 further including adhesive means for sealing said overcap ring to said container.

7. The system defined in claim 6 further including a doublewall corrugated carton.

8. The system defined in claim 6 further including a top end cap and a bottom end cap in said carton, said end caps being formed of polystyrene foam.

9. The system defined in claim 8 further including adhesive means for holding said corrugated carton closed.

10. The system defined in claim i wherein said bottle is formed of high density polyethylene.

11. The system defined in claim 1 wherein said closure element includes a screw thread.

12. The system defined in claim 1 wherein said means for attaching said lid to said outer container includes friction fitting elements on said lid and on said outer container.

13. The system defined in claim 1 wherein said collapsible top wall includes a plurality of ribs extending radially from said neck to said sidewall.

14. The system defined in claim 1 wherein said central section includes a plurality of channels extending radially from said opening.

15. The system defined in claim 1 wherein said bottle is one-piece and is formed of plastic, and said outer container is unitary and is formed of metal.

16. A system for containing and disposing medical waste/infectious material comprising:

A) a one-piece plastic bottle means for containing medical waste, such as needles and sharps, and having a neck through which the medical waste is inserted into said bottle, said one-piece bottle having a resistance to pressure inside said bottle when said neck is closed;

B) a metal container means for enclosing and reinforcing said bottle and having an impact and a penetration resistance, said container securely holding said bottle, said bottle means reinforcing said container, whereby said bottle and said container support and reinforce each other;

C) bottle closure means for closing said neck including one-way means for permitting the medical waste to enter said bottle and for resisting movement of the medical waste out of said bottle via said neck; and D) container closure means for closing said container with said bottle in said container, said container closure means including an insert element having a neck-receiving opening defined therethrough and covering said plastic bottle with said neck being accommodated through said neck-receiving opening when said insert element is in place in said metal container.

17. The system defined in claim 16 wherein said bottle has a sidewall and said container has a sidewall, said bottle sidewall abutting said container sidewall for reinforcing both of said sidewalls.

18. The system defined in claim 17 wherein said neck has an outer dimension that is much smaller than an outer dimension of said bottle adjacent to said neck.

19. The system defined in claim 16 wherein said container closure means further includes a lid and means for attaching said lid to said metal container in covering relationship to said insert element.

20. The system defined in claim 19 wherein said container closure means further includes an overcap ring and means for attaching said overcap ring on said metal container in covering relationship to said lid.

* * * * *